United States Patent
LeBoeuf et al.

(10) Patent No.: US 6,313,187 B2
(45) Date of Patent: Nov. 6, 2001

(54) HIGH REFRACTIVE INDEX OPHTHALMIC DEVICE MATERIALS PREPARED USING A POST-POLYMERIZATION CROSS-LINKING METHOD

(75) Inventors: Albert R. LeBoeuf, Burleson; Douglas C. Schlueter; Joseph I. Weinschenk, III, both of Fort Worth, all of TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/766,493

(22) Filed: Jan. 19, 2001

Related U.S. Application Data

(63) Continuation-in-part of application No. 09/283,592, filed on Apr. 1, 1999, now abandoned.
(60) Provisional application No. 60/081,874, filed on Apr. 15, 1998.

(51) Int. Cl.[7] ................. C08F 2/48; C08F 4/32; C08F 4/34; C08J 5/00
(52) U.S. Cl. ............ 522/13; 522/182; 522/183; 522/184; 523/106; 526/232
(58) Field of Search .............. 522/13, 182, 183, 522/184; 523/106; 526/232

(56) References Cited

U.S. PATENT DOCUMENTS

| | | | |
|---|---|---|---|
| 4,620,954 | 11/1986 | Singer et al. | 264/1.4 |
| 4,919,850 | 4/1990 | Blum et al. | 264/1.4 |
| 4,921,205 | 5/1990 | Drew, Jr. et al. | 249/61 |
| 5,224,957 | 7/1993 | Gasser et al. | 623/6 |
| 5,290,892 | 3/1994 | Namdaran et al. | 526/259 |
| 5,331,073 | * 7/1994 | Weinschenk, III et al. | |
| 5,374,663 | 12/1994 | Daicho et al. | 523/106 |
| 5,403,901 | * 4/1995 | Namdaran et al. | |

FOREIGN PATENT DOCUMENTS

| | | |
|---|---|---|
| 0 308 130A2 | 3/1989 | (EP) . |
| 0 345 994 A2 | 12/1989 | (EP) . |
| 0 514 096 A2 | 11/1992 | (EP) . |
| 2 765 583 | 1/1999 | (FR) . |
| WO 94/11764 | 5/1994 | (WO) . |
| WO 96/28762 | 9/1996 | (WO) . |
| WO 97/09170 | 3/1997 | (WO) . |
| WO 97/24382 | 8/1997 | (WO) . |

OTHER PUBLICATIONS

"Peroxides" Product Information from Hercules Incorporated, Wilmington, DE.

"Di–Cup" Product Information from Hercules Incorporated, Wilmington, DE.

Koch, D. Foldable Intraocular Lenses, Slack Incorporated, Thorofare, NJ, (1993), Chapter 8, "Alcon AcrySof™ Acrylic Intraocular Lens," pp. 161–177.

* cited by examiner

*Primary Examiner*—Tae H. Yoon
(74) *Attorney, Agent, or Firm*—Patrick M. Ryan

(57) ABSTRACT

Acrylic, high refractive index ophthalmic device materials comprising an aryl acrylic monomer, a first stage polymerization initiator and a second stage cross-linking agent are prepared in a two-stage method. The monomers used to form the ophthalmic device materials do not contain cross-linking agents having more than one unsaturated bond. In the first stage of the method, the materials are polymerized. In the second stage, the materials are cross-linked by exposure to heat.

3 Claims, No Drawings

HIGH REFRACTIVE INDEX OPHTHALMIC DEVICE MATERIALS PREPARED USING A POST-POLYMERIZATION CROSS-LINKING METHOD

This application is a continuation-in-part application of co-pending U.S. patent application Ser. No. 09/283,592, filed Apr. 1, 1999, now abandoned which claims priority from U.S. Provisional Patent Application Ser. No. 60/081,874, filed Apr. 15, 1998.

FIELD OF THE INVENTION

This invention relates to a method of preparing high refractive index ophthalmic device materials. In particular, the present invention relates to a two-stage method in which ophthalmic device materials are first polymerized and then cross-linked.

BACKGROUND OF THE INVENTION

The two most common types of polymerization initiators for ophthalmic device materials are thermal initiators and photoinitiators. Typical thermal initiators, including free radical initiators such as peroxides, initiate polymerization as temperature is increased. In some cases, two or three temperature tiers are involved such that curing involves a schedule of temperature/time combinations. Thermal initiation generally requires holding the monomer composition at elevated temperatures for lengthy periods of time. Total cure times of twenty-four hours are not unusual. See, for example, U.S. Pat. No. 5,290,892.

Photoinitiators generally offer the advantage of relatively short cure times and, unlike thermal initiators, can be used at ambient conditions, eliminating the need for high-temperature equipment or special ovens. Photoinitiators are activated by radiation of one or more specified wavelengths, rather than heat. Photoinitiation of ophthalmic lens materials is known. See, for example, U.S. Pat. No. 5,290,892.

The most common types of photoinitiators known or used for curing ophthalmic lens polymers are probably UV-sensitive photoinitiators. UV-sensitive photoinitiators are, however, generally not suitable for use with lens materials that contain a UV-absorbing chromophore. UV-absorbing chromophores present in an ophthalmic lens composition can interfere with the ability of UV-sensitive photoinitiators to efficiently cure the composition. Today, UV-absorbing chromophores are frequently incorporated in ophthalmic lens materials in order to reduce or block UV light from reaching the retina. Although methods are known for temporarily "blocking" UV absorbing chromophores during processing, thereby preventing interference with a UV-initiator, these methods require that the UV-absorber be "un-blocked" after the composition is cured. The UV chromophore can be "un-blocked" by either chemical or thermal means. "Un-blocking" is generally complicated and can add 4–6 hours to processing times, offsetting some or all of the time advantages offered by photoinitators.

In addition to UV-sensitive photoinitiators, visible-light initiators are also known. For example, U.S. Pat. No. 5,224,957 discloses photopolymerizable compositions useful in forming an intraocular lens in situ. The compositions are delivered into the natural lens capsule or a thin plastic shell substitute and then polymerized. The reference compositions contain 90–99.99% by weight of at least one polyfunctional acrylic and/or methacrylic acid ester. Suitable acid esters include bisphenol A or bishydroxypolyalkoxy bisphenol A derivatives lengthened with ethylene oxide or propylene oxide. The compositions of the '957 patent are cured using photoinitiators which absorb light in the range 400–500 nm. Suitable initiators include alpha-diketones, in particular camphorquinone, benzil and phenanthrene quinone, and mono and bisacylphosphine oxides.

International Patent Application Publication No. WO 96/28762 also discloses photocurable compositions comprising acrylic components. The compositions contain specified amounts of di(meth)acrylates, poly(meth)acrylates, urethane(meth)acrylates, and oligomeric di(meth)acrylates based on bisphenol A or bisphenol F. The photoinitiator may be "any photoinitiator which forms free radicals when irradiated suitably." Suitable classes include benzoin ethers; acetophenones; benzil; anthraquinones; benzoylphosphine oxides (e.g., 2,4,6-trimethylbenzoyldiphenylphosphine oxide); benzophenones. Photoinitiators particularly suitable for use with argon ion lasers include 2,4,6-trimethylbenzoyldiphenylphosphine oxide.

Some ophthalmic devices are obtained by a monomer cast polymerization method. In such a method, the monomer solution is cast directly into a mold of desired shape and then polymerized or cured, followed by any machining or polishing, etc. See, for example, U.S. Pat. Nos. 4,921,205 and 5,290,892.

In other cases, ophthalmic device materials are formed by first preparing a "prepolymer" or partially cured material, followed by further curing. See, for example, U.S. Pat. No. 5,374,663 describing a prepolymer process for producing a U.V. absorber-containing intraocular lens material in which a monomer solution comprising a lens-forming monomer, an U.V. absorber and a polymerization initiator is introduced into a reactor and heated for a length of time and at a temperature sufficient to obtain a prepolymer of high viscosity. Thereafter, the prepolymer is filtered, cast into a cell or mold and further heated for a time at a temperature sufficient to obtain a transparent lens material.

According to the '663 patent, the prepolymer process has the advantage that the prepolymer scarcely leaks out of the cell or mold because of its high viscosity, and that the degree of shrinkage in the step of obtaining a lens material from the prepolymer is small. On the other hand, the prepolymer process has some problems as well, including (i) the control of the polymerization degree and viscosity of the prepolymer obtained in the first polymerization step, and (ii) when a cross-linking monomer is contained in the material, an insoluble polymer is formed in the prepolymer step, making any filtration treatment difficult or impossible, and the polymer produced after the further curing step becomes "non-uniform."

SUMMARY OF THE INVENTION

The present invention relates to a method for preparing acrylic, high refractive index ophthalmic device materials. The ophthalmic device materials comprise at least one aryl acrylic hydrophobic monomer, a first stage polymerization initiator selected from the group consisting of photoinitiators and thermal free radical initiators having a ten hour half-life ("10 hr $t_{1/2}$") of about 50° C. or less, and a second stage cross-linking agent. If the first stage initiator is a photoinitiator, the second stage cross-linking agent is a thermal free radical initiator having a 10 hr $t_{1/2}$ of about 50° C. or greater. If the first stage initiator is a thermal free radical initiator having a 10 hr $t_{1/2}$ of about 50° C. or less, the second stage cross-linking agent is a thermal free radical initiator having a 10 hr $t_{1/2}$ of about 65° C. or greater. The monomers used to form the ophthalmic device materials do not contain any ingredient having more than one unsaturated site, as such ingredients will cause premature cross-linking.

According to the present invention, the ophthalmic device material is prepared using a two-stage process. In the first stage, the material is polymerized such that the second stage cross-linking agent is not activated. In the second stage, the material is cross-linked by activating the second stage cross-linking agent. The two-stage process of the present invention can provide enhanced control of material shrinkage and stress problems associated with cast molding operations compared to single stage curing processes.

DETAILED DESCRIPTION OF THE INVENTION

As used herein, "high refractive index" means a refractive index of about 1.50 or greater when measured at room temperature using an Abbe' refractometer at 589 nm (Na light source).

According to the present invention, acrylic, high refractive index ophthalmic device materials are prepared in two stages. In the first stage, the device material is polymerized. In the second stage, the device material is cross-linked.

The ophthalmic device materials of the present invention comprise at least one compound of Formula I below.

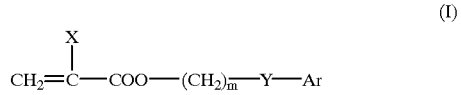

(I)

wherein:

X is H or $CH_3$;

m is 0–10;

Y is nothing, O, S, or NR wherein R is H, $CH_3$, $C_nH_{2n+1}$ (n=1–10) iso $OC_3H_7$, $C_6H_5$, or $CH_2C_6H_5$;

Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$.

Monomers of Formula I are known and include, but are not limited to: 2-phenoxyethyl acrylate; 2-phenylethylthio acrylate; 2-phenylethylamino acrylate; phenyl acrylate; benzyl acrylate; 2-phenylethyl acrylate; 3-phenylpropyl acrylate; 3-phenoxypropyl acrylate; 4-phenylbutyl acrylate; 4-phenoxybutyl acrylate; 4-methylphenyl acrylate; 4-methylbenzyl acrylate; 2-2-methylphenylethyl acrylate; 2-3-methylphenylethyl acrylate; 2-4-methylphenylethyl acrylate; and their corresponding methacrylate compounds. These acrylic/methacrylic monomers and others are disclosed in U.S. Pat. No. 5,290,892, the entire contents of which are hereby incorporated by reference.

Preferred monomers of Formula (I) are those where m is 2–4; Y is nothing or O; and Ar is phenyl. Most preferred are 2-phenylethyl acrylate, 2-phenoxyethyl acrylate, 3-phenylpropyl acrylate, 3-phenoxypropyl acrylate, 4-phenylbutyl acrylate, and 4-phenoxybutyl acrylate, and their corresponding methacrylate compounds.

The ophthalmic device materials of the present invention preferably contain at least two monomers of Formula I, wherein at least one is a methacrylate monomer (X=$CH_3$) and at least one is an acrylate monomer (X=H). The exact amount of monomer of Formula I present in the acrylic, high refractive index ophthalmic device materials of the present invention will vary depending upon the identity of the monomer(s) of Formula I, the identity of any other device-forming monomer(s) present in the materials, and the desired mechanical properties. For example, foldable intraocular lenses are preferably made from polymers having a glass transition temperature no greater than normal room temperature, e.g., about 20–25° C., in order that the lenses can be rolled or folded conveniently at room temperature. Materials having a glass transition temperature of about 15° C. or less are even more preferred for foldable intraocular lens applications. Glass transition temperature is determined at room temperature using a differential scanning calorimeter at a heating rate of 10° C./min.

Additionally, materials exhibiting an elongation of at least 150% when measured at room temperature using an Instron tensile tester at a cross-head speed of 50 cm/min are preferred for use in foldable intraocular lenses because such lenses must exhibit sufficient strength to allow them to be folded without fracturing. For foldable intraocular lens applications, polymers having an elongation of at least 200% are more preferred.

In general, the acrylic, high refractive index ophthalmic device materials of the present invention preferably contain at least 50% (w/w) of monomer(s) of Formula I. In a more preferred embodiment, the device materials will contain one or more monomers of Formula I in an amount totaling 70% (w/w) or more, and most preferably, 80% (w/w) or more.

Device-forming monomers other than those of Formula I optionally may be included in the materials of the present invention. Many such ophthalmic device-forming monomers are known. Any known device-forming monomer may be used if it is compatible with the monomer(s) of Formula I present in the ophthalmic device material and does not prevent the ability of the stage 1 polymerization initiator to cure the material such that the material contains no cross-linking or is substantially free of cross-linking. Suitable device-forming monomers other than those of Formula I include, but are not limited to: $C_1$–$C_8$ alkylacrylates, $C_1$–$C_8$ cycloalkylacrylates, N-alkylacrylamides (where alkyl=$C_1$–$C_4$), phenoxyalkylacrylates (where alkyl=$C_1$–$C_8$), and their corresponding methacrylates. Suitable device-forming monomers other than those of Formula I also include N-vinylpyrrolidone. See U.S. Pat. No. 5,331,073, the entire contents of which are hereby incorporated by reference, for examples of device-forming materials other than those of Formula 1.

As in the case of the monomer(s) of Formula I, the amount of any other device-forming monomers present in the ophthalmic device materials of the invention will vary depending upon the identity of the monomer(s) of Formula I, the identity of the optional device-forming monomer(s), and the mechanical properties desired for the finished ophthalmic material. In general, for foldable intraocular lens applications, the ophthalmic device materials of the present invention preferably contain about 45% (w/w) or less, and more preferably about 30% (w/w) or less, of device-forming monomers other than those of Formula I.

The ophthalmic device materials also comprise a first stage polymerization initiator selected from the group consisting of photoinitiators and thermal free radical initiators having a 10 hr $t_{1/2}$ of about 55° C. or less, preferably about 50° C. or less. Suitable photoinitiators include, but are not limited to, UV- and blue-light photoinitiators. Many such photoinitiators are known. Preferred blue-light photoinitiators are benzoylphosphine oxide initiators, such as 2,4,6-trimethyl-benzoyldiphenylophosphine oxide; bis-(2,6-dichlorobenzoyl)-4-N-propylphenyl-phosphine oxide; and bis-(2,6-dichlorobenzoyl)-4-N-butylphenylphosphine oxide. Most preferred is 2,4,6-trimethyl-benzoyldiphenylophosphine oxide, commercially available as Lucirin® TPO from BASF Corporation (Charlotte, N.C.). See, for example, U.S. Pat. No. 5,891,931, the entire contents of which are hereby incorporated by reference.

Many thermal free radical initiators having a 10 hr $t_{1/2}$ of about 55° C. or less are known, including but not limited to, both peroxide- and azo-type compounds. Suitable peroxide- and azo-type compounds include, for example, those having a 10 hr $t_{1/2}$ of about 55° C. or less that are listed in Tables 1 and 2 below.

The amount of the first stage polymerization initiator in the device materials of the present invention will depend upon the identity of the other ingredients in the materials, the curing conditions, etc. In general, however, the amount of first stage polymerization initiator contained in the mixture to be polymerized in stage 1 of the present invention will be about 3% (w/w) or less, preferably about 2% (w/w) or less, and most preferably about 1% (w/w).

In addition to the device-forming monomer(s) (i.e., monomers of Formula I and any other device forming monomers) and the first stage polymerization initiator, the ophthalmic device materials of the present invention contain a second stage cross-linking agent. If the first stage initiator is a photoinitiator, the second stage cross-linking agent is a thermal free radical initiator having a 10 hr $t_{1/2}$ of about 50° C. or greater. If the first stage initiator is a thermal free radical initiator having a 10 hr $t_{1/2}$ of about 55° C. or less, the second stage cross-linking agent is a thermal free radical initiator having a 10 hr $t_{1/2}$ of about 65° C. or greater, preferably about 70° C. or greater. Many free radical initiators having a 10 hr $t_{1/2}$ of about 50° C. or greater are known, including but not limited to the peroxide- and azo-type compounds that are listed in Tables 1 and 2 below. Dicumyl peroxide is the preferred second stage cross-linking agent for use with ophthalmic device materials comprising 2-phenylethyl acrylate and 2-phenylethyl methacrylate.

The amount of the second stage cross-linking agent contained in the device materials of the present invention will depend upon, among other factors, the degree of cross-linking desired. In general, however, the amount of second stage cross-linking agent in the ophthalmic device materials will be about 2–5% (w/w), and preferably about 2.5–4% (w/w).

In order to prevent premature cross-linking, the ophthalmic device materials of the present invention do not contain any ingredient having more than one unsaturated bond. Such ingredients include the common cross-linking monomers ethyleneglycol dimethacrylate; diethylene glycol dimethacrylate; ethyleneglycol diacrylate; allyl methacrylates; allyl acrylates; 1,3-propanediol dimethacrylate; 1,6-hexanediol dimethacrylate; 1,4-butanediol dimethacrylate; polyethyleneoxide mono- and diacrylates; and the like.

Ultraviolet absorbing chromophores are optionally included in the ophthalmic device materials of the present invention. Such chromophores prevent or inhibit UV light from damaging the eye. The ultraviolet absorbing chromophore in the device material of the present invention can be any compound which absorbs light having a wavelength shorter than about 400 nm, but does not absorb any substantial amount of visible light, and which is compatible with the device-forming monomer(s) present in the material. The ultraviolet absorbing compound is incorporated into the monomer mixture and is entrapped in the polymer matrix when the monomer mixture is polymerized. Suitable ultraviolet absorbing compounds include substituted benzophenones, such as 2-hydroxybenzophenone, and 2-(2-hydroxyphenyl)-benzotriazoles. It is preferred to use an ultraviolet absorbing compound that is copolymerizable with the device-forming monomers described above so that it will be covalently bound to the polymer matrix. In this way, possible leaching of the ultraviolet absorbing compound out of the device and into the interior of the eye is minimized. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5'-methyl phenyl) benzotriazole.

If the ophthalmic device material does include a UV-absorber, it is unlikely that a UV polymerization initiator may be used as the first stage polymerization initiator. In such cases, the first stage polymerization initiator will likely have to be thermal initiator having a 10 hr $t_{1/2}$ of about 55° C. or less or a blue-light initiator in order to avoid interference with the UV-absorber.

Blue-light absorbing compounds are also optionally included in the device materials of the present invention. If a blue-light absorbing compound, e.g. a yellow dye, is included in the device material of the present invention, then the first stage polymerization initiator will likely not be a blue-light photoinitiator. In the event the device material contains both a UV-absorber and a blue-light absorbing compound, the first stage polymerization initiator will likely be a low temperature thermal initiatior. Preferably, blue-light absorbers are copolymerizable with the device-forming monomers. Suitable polymerizable blue-light blocking chromophores include those disclosed in U.S. Pat. No. 5,470, 932.

The device materials of this invention are prepared by forming a mixture comprising the device-forming monomer (s) (monomer(s) of Formula I and any optional device-forming monomer(s)), the first stage polymerization initiator and the second stage cross-linking agent, along with any UV- or blue-light absorbing compounds and any other suitable ingredients, in the desired proportions. The mixture can then be introduced into a mold of desired shape to form an ophthalmic device. Alternatively, the mixture can be cast in sheets from which the finished form can be obtained by compression molding (generally with mild pre-heating).

In either case (direct cast molding in final form or casting in sheets for subsequent molding), the ophthalmic device material is polymerized in the first stage of the present invention by activating the first stage polymerization initiator (e.g., using heat, UV- or blue-light). In the case where the first stage polymerization initiator is a low temperature thermal initiator and the second stage cross-linking agent is dicumyl peroxide, the thermal initiator may be activated by exposure to temperatures of up to approximately 55° C. or so without activating the dicumyl peroxide. The curing parameters, e.g., length of exposure and temperature or intensity of light source, are preferably chosen to accomplish complete polymerization.

After the ophthalmic device material is polymerized in stage 1, it is cross-linked in stage 2 of the present invention. Cross-linking is achieved by activating the second stage cross-linking agent using heat. The temperature and length of exposure to heat are determined by the identity and amount of the second stage cross-linking agent and the desired degree of cross-linking to be achieved (i.e., the desired physical properties of the ophthalmic device materials). In the case where the second stage cross-linking agent is dicumyl peroxide, the activation temperature will be about 115° C. or greater. The duration of heating to achieve the second-stage cross-linking is preferably about four times the half-life of the second stage cross-linking agent at the chosen activation temperature. In the case of dicumyl peroxide and an activation temperature of approximately 135° C., the duration of heating is approximately 4 hours.

The ophthalmic device materials prepared according to the present invention may be used to make almost any type of ophthalmic lens, including contact lenses, intracorneal lenses and intraocular lenses. Ophthalmic lenses constructed of the disclosed materials can be of any design, but are preferably intraocular lenses (IOLs) capable of being rolled or folded and inserted through a relatively small incision. For example, the IOLs can be of what is known as a one piece or multipiece design. Typically, an IOL comprises an optic and at least one haptic. The optic is that portion which serves as the lens and the haptics are attached to the optic and are like arms that hold the optic in its proper place in the eye. The optic and haptic(s) can be of the same or different material. Haptics may be attached to the optic using conventional techniques. In a single piece lens, the optic and the haptics are formed out of one piece of material. Depending on the material, the haptics are then cut, or lathed, out of the material to produce the IOL. In addition to ophthalmic lenses, the materials prepared according to the methods of the present invention may also be used to make other ophthalmic devices including, but not limited to, keratoprostheses and corneal inlays or rings.

Molding and drilling operations are easily carried out if the device, e.g., an IOL optic, is molded between two polypropylene mold halves. The mold containing the cured device material is then placed on a lathe and cut to the desired shape. The mold may then be easily mounted to carry out any drilling operations prior to removing the mold halves. Both the lathing and drilling operations may be facilitated by cooling the mold/device in a freezer to less than 10° C. and preferably less than 0° C. prior to each of these operations. If premature release of one or both mold halves occurs, it may be necessary to use clamps or alternative mold materials or to pretreat the surface of the mold halves.

TABLE 1

Peroxide initiators (Solvent = 0.2 M benzene)

| Name | 10 hr $t_{1/2}$ (° C.) |
|---|---|
| Diacyl peroxides | |
| dibenzoyl peroxide (BPO) | 73 |
| di(2,4-dichlorobenzoyl) peroxide | 54 |
| diacetyl peroxide | 69 |
| dilauroyl peroxide | 62 |
| Peroxyesters | |
| t-butyl perbenzoate | 105 |
| t-butyl peracetate | 102 |
| 2,5-di(benzoylperoxy)-2,5-dimethylhexane | 100 |
| di-t-butyl diperoxyazelate | 99 |
| t-butyl peroxy-2-ethyl-hexanoate | 73 |
| t-amyl peroctoate | 70 |
| t-butyl peroxyneodecanoate | 47 |
| Peroxydicarbonates | |
| di(n-propyl)peroxydicarbonate (Lupersol 221) | 50 |
| di(4-t-butylcyclohexyl)peroxydicarbonate | 43 |
| Diperoxyketals | |
| ethyl 3,3-di(t-butylperoxy)butyrate | 111 |
| 2,2-di(t-butylperoxy)-butane | 104 |
| 2,2-di(t-butylperoxy)-4-methylpentane | 101 |
| 1,1-di(t-butylperoxy)-cyclohexane | 95 |
| 1,1-di(t-butylperoxy)-3,3,5-trimethyl-cyclohexane | |
| Dialkyl peroxides | |
| dicumyl peroxide | 115 |
| di-t-butyl peroxide | 126 |
| 2,6-di(t-butylperoxy)-2,5-dimethylhexane | 119 |

TABLE 2

Azo initiators

| Name | Wako Product No.* | 10 hr $t_{1/2}$ (° C.) | solvent |
|---|---|---|---|
| 10 hr $t_{1/2}$ ≦65° C. | | | |
| 2,2'-azobisisobutyronitrile (AIBN) | V-60 | 65 | toluene |
| 2,2'-azobis(2,4-dimethyl-valero-nitrile) | V-65 | 51 | toluene |
| 2,2'-azobis(4-methoxy-2,4-dimethylvaleronitrile) | V-70 | 30 | toluene |
| 2,2'-azobis(N,N'-dimethylene-isobutyramidine)dihydrochloride | VA-044 | 44 | water |
| 2,2'-azobis(2-amidino-propane)-dihydrochloride | V-50 | 56 | water |
| 2,2'-azobis(N,N'-dimethylene-isobutyramidine) | VA-061 | 61 | methanol |
| 10 hr $t_{1/2}$ >65° C. | | | |
| dimethyl-2,2'-azobisisobutyate | V-601 | 66 | toluene |
| 2,2'-azobis(2-methylbutyronitrile) | V-59 | 67 | toluene |
| 1,1'-azobis(1-cyclohexanecarbo-nitrile) | V-40 | 88 | toluene |
| 2-(carbamoylazo)-isobutyronitrile | V-30 | 104 | toluene |
| 2,2'-azobis(2,4,4-trimethyl-pentane) | VR-110 | 110 | diphenylether |
| 2-phenylazo-2,4-dimethyl-4-methoxyvaleronitrile | V-19 | 122 | xylene |
| 2,2'-azobis(2-methylpropane) | VR-160 | 160 | gas phase |
| 4,4'-azobis(4-cyanopentanoic acid) | V-501 | 69 | water |
| 2,2'-azobis{2-methyl-N-[1,1-bis-(hydroxymethyl)-2-hydroxyethyl]-propionamide} | VA-080 | 80 | water |
| 2,2'-azobis{2-methyl-N-[1,1-bis-(hydroxymethyl)ethyl]propion-amide} | VA-082 | 82 | water |
| 2,2'-azobis[2-methyl-N-(2-hydroxyethyl)propionamide] | VA-086 | 86 | water |
| 2,2'-azobis(isobutyramide)-dihydrate | VA-088 | 88 | water |

*Wako Chemicals USA, Inc. (Richmond, Virginia)

The invention will be further illustrated by the following examples which are intended to be illustrative, but not limiting.

EXAMPLES

The ophthalmic device materials shown below in Table 3 were prepared as follows:

Example 1 was prepared by heating at 70° C. for 7 hours, followed by heating at 100° C. for 7 hours.

Example 2 was prepared by heating at 135° C. for 17.5 hours.

Examples 3–14 were prepared using the two-stage method of the present invention. In stage 1, the ingredients were mixed, transferred to 1-mm thick, slab, polypropylene mold, and polymerized by exposure to blue light (Palatray CU/14 mW/cm$^2$) for 15 minutes. In stage 2, the materials remained in the same slab molds and were cross-linked by heating at 135 C. for 4, 6 or 10 hours as indicated.

In all cases (Examples 1–14) the ophthalmic device materials were vacuum degassed for approximately 10 minutes immediately prior to filling and sealing the polypropylene slab molds.

The amount of each of the ingredients is expressed in % w/w.

TABLE 3

|  | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| PEA | 65 | 65 | 65 | 65 | 65 | 60 | 60 | 60 | 55 | 55 | 55 | 50 | 50 | 50 |
| PEMA | 30 | 30 | 30 | 30 | 30 | 35 | 35 | 35 | 40 | 40 | 40 | 45 | 45 | 45 |
| oMTP | 1.8 | 1.8 | 1.8 | 1.8 | 1.8 | 1.8 | 1.8 | 1.8 | 1.8 | 1.8 | 1.8 | 1.8 | 1.8 | 1.8 |
| Lucirin TPO | — | 0.5 | 0.5 | 0.5 | 0.5 | 0.5 | 0.5 | 0.5 | 0.5 | 0.5 | 0.5 | 0.5 | 0.5 | 0.5 |
| DiCuP | — | 4 | 4 | 4 | 4 | 4 | 4 | 4 | 4 | 4 | 4 | 4 | 4 | 4 |
| BDDA | 3.2 | — | — | — | — | — | — | — | — | — | — | — | — | — |
| Perkadox-16 | 1.8 | — | — | — | — | — | — | — | — | — | — | — | — | — |
| Cure hrs @ 135 C. | — | 17.5 | 4 | 6 | 10 | 4 | 6 | 10 | 4 | 6 | 10 | 4 | 6 | 10 |
| Tg (° C.) | — | 14.7 | 0.0 | 4.3 | 0.2 | 5.5 | 3.8 | 3.6 | 6.9 | 3.5 | 5.9 | 6.3 | 7.9 | 9.1 |
| % Acetone uptake | — | 53.9 | 60.2 | 58.3 | 54.6 | 59.1 | 55.9 | 55.5 | 61.3 | 59.0 | 56.8 | 62.3 | 59.7 | 57.9 |
| % Acetone extractables | — | 4.56 | 4.98 | 4.96 | 3.75 | 4.69 | 5.04 | 4.56 | 6.15 | 4.66 | 4.38 | 6.44 | 5.50 | 5.15 |
| Stress (psi) | 1200 | — | 1120 | 1176 | 959 | 1250 | 1183 | 1115 | 1203 | 1252 | 1278 | 1148 | 1332 | 1279 |
| % Strain | 600 | — | 1440 | 1236 | 965 | 1215 | 1156 | 952 | 1096 | 963 | 872 | 648 | 676 | 654 |
| Modulus, secant (psi) | 300 | — | 227 | 218 | 203 | 391 | 340 | 352 | 572 | 676 | 554 | 1038 | 1073 | 1040 |
| Modulus, Young (psi) | — | — | 452 | 410 | 327 | 810 | 760 | 645 | 1164 | 1247 | 1049 | 1828 | 1892 | 1837 |

PEA = 2-phenylethylacrylate
PEMA = 2-phenylethylmethacrylate
oMTP = o-Methallyl Tinuvin P(2-(3'-methallyl-2'-hydroxy-5'-methyl phenyl)-benzotriazole)
Lucirin TPO = 2,4,6-trimethyl-benzoyldiphenylophosphine oxide
BDDA = 1,4-butanediol diacrylate
DiCuP = dicumyl peroxide
Perkadox 16 = di-(4-tert-butylcyclohexyl)peroxydicarbonate The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A two-stage method for preparing an acrylic, high refractive index ophthalmic device material, wherein the ophthalmic device material comprises (i) at least two aryl acrylic hydrophobic monomers of the formula

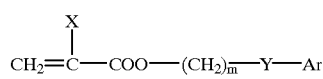

(I)

wherein:
   X is H or $CH_3$;
   m is 0–10;
   Y is nothing, O, S, or NR wherein R is H, $CH_3$, $C_nH_{2n+1}$ (n=1–10) iso $OC_3H_7$, $C_6H_5$, or $CH_2C_6H_5$;
   Ar is any aromatic ring which can be unsubstituted or substituted with $CH_3$, $C_2H_5$, n-$C_3H_7$, iso-$C_3H_7$, $OCH_3$, $C_6H_{11}$, Cl, Br, $C_6H_5$, or $CH_2C_6H_5$;
   and further wherein at least one of the aryl acrylic hydrophobic monomers is a methacrylate monomer and at least one of the aryl acrylic hydrophobic monomers is an acrylate monomer;

(ii) a first stage polymerization initiator selected from the group consisting of photoinitiators and thermal free radical initiators having a 10 hr $t_{1/2}$ of about 55° C. or less; and (iii) a second stage cross-linking agent where the second stage cross-linking agent is a thermal free radical initiator having a 10 hr $t_{1/2}$ of about 50° C. or greater if the first stage polymerization initiator is a photoinitiator and the second stage cross-linking agent is a thermal free radical initiator having a 10 hr $t_{1/2}$ of about 65° C. or greater if the first stage polymerization initiator is a thermal free radical initiator having a 10 hr $t_{1/2}$ of about 55° C. or less, wherein the first stage of the method comprises polymerizing the ophthalmic device material by activating the first stage polymerization initiator without activating the second stage cross-linking agent; and the second stage of the method comprises cross-linking the ophthalmic device material by activating the second stage cross-linking agent.

2. The method of claim 1 wherein the ophthalmic device materials comprise a total of at least 50% (w/w) of aryl acrylic hydrophobic monomers of Formula (I).

3. The method of claim 2 wherein the ophthalmic device materials comprise a total of at least 70% (w/w) of aryl acrylic hydrophobic monomers of Formula (I).

* * * * *